(12) United States Patent
Abraham-Fuchs et al.

(10) Patent No.: US 9,218,584 B2
(45) Date of Patent: Dec. 22, 2015

(54) METHOD AND SYSTEM FOR MEASURING QUALITY OF PERFORMANCE AND/OR COMPLIANCE WITH PROTOCOL OF A CLINICAL STUDY

(71) Applicants: Klaus Abraham-Fuchs, Erlangen (DE); Gudrun Zahlmann, Neumarkt (DE); Rainer Kuth, Herzogenaurach (DE); Eva Rumpel, Erlangen (DE); Siegfried Schneider, Erlangen (DE); Markus Schmidt, Nuremberg (DE); Horst Schreiner, Fuerth (DE)

(72) Inventors: Klaus Abraham-Fuchs, Erlangen (DE); Gudrun Zahlmann, Neumarkt (DE); Rainer Kuth, Herzogenaurach (DE); Eva Rumpel, Erlangen (DE); Siegfried Schneider, Erlangen (DE); Markus Schmidt, Nuremberg (DE); Horst Schreiner, Fuerth (DE)

(73) Assignee: Siemens Aktiengesellschaft, Munich (DE)

( * ) Notice: Subject to any disclaimer, the term of this patent is extended or adjusted under 35 U.S.C. 154(b) by 95 days.

(21) Appl. No.: 13/895,490

(22) Filed: May 16, 2013

(65) Prior Publication Data
US 2013/0253944 A1    Sep. 26, 2013

Related U.S. Application Data

(62) Division of application No. 10/975,011, filed on Oct. 28, 2004, now Pat. No. 8,515,774.

(60) Provisional application No. 60/545,164, filed on Feb. 18, 2004.

(51) Int. Cl.
| | | |
|---|---|---|
| *G06Q 10/00* | (2012.01) | |
| *G06Q 50/00* | (2012.01) | |
| *G06Q 10/06* | (2012.01) | |
| *G06F 19/00* | (2011.01) | |
| *G06Q 50/22* | (2012.01) | |
| *G06Q 30/00* | (2012.01) | |

(52) U.S. Cl.
CPC ........ *G06Q 10/06393* (2013.01); *G06F 19/327* (2013.01); *G06F 19/366* (2013.01); *G06Q 30/018* (2013.01); *G06Q 50/22* (2013.01); *G06F 19/363* (2013.01)

(58) Field of Classification Search
CPC .............................. G06Q 50/22; G06Q 50/24
USPC ........................................................ 705/2–3
See application file for complete search history.

(56) References Cited

U.S. PATENT DOCUMENTS

| | | | |
|---|---|---|---|
| 2002/0002474 | A1 | 1/2002 | Michelson et al. |
| 2002/0143563 | A1* | 10/2002 | Hufford et al. ................... 705/1 |
| 2003/0065669 | A1* | 4/2003 | Kahn et al. .................... 707/100 |

(Continued)

FOREIGN PATENT DOCUMENTS

WO    WO 2005/079660    9/2005

OTHER PUBLICATIONS

Office Action for corresponding U.S. Appl. No. 13/895,566 dated Sep. 10, 2013.

(Continued)

*Primary Examiner* — Joseph Burgess
(74) *Attorney, Agent, or Firm* — Harness, Dickey & Pierce, P.L.C.

(57) ABSTRACT

A method is proposed for determining clinical study compliance. The method includes obtaining criteria for the clinical study and accessing stored clinical data relating to the clinical study. Thereafter, the criteria and clinical data are correlated to determine a measure of compliance with the criteria of the clinical study.

17 Claims, 2 Drawing Sheets

(56) References Cited

U.S. PATENT DOCUMENTS

| | | |
|---|---|---|
| 2004/0243439 A1 | 12/2004 | Huggard et al. |
| 2004/0249664 A1* | 12/2004 | Broverman et al. .............. 705/2 |
| 2005/0182658 A1 | 8/2005 | Abraham-Fuchs et al. |
| 2005/0182663 A1 | 8/2005 | Abraham-Fuchs et al. |
| 2005/0182664 A1 | 8/2005 | Abraham-Fuchs et al. |
| 2005/0182665 A1 | 8/2005 | Abraham-Fuchs et al. |
| 2006/0143047 A1* | 6/2006 | Briegs et al. ...................... 705/2 |
| 2007/0142979 A1 | 6/2007 | Abraham-Fuchs et al. |
| 2007/0143146 A1 | 6/2007 | Abraham-Fuchs et al. |
| 2007/0143691 A1 | 6/2007 | Abraham-Fuchs et al. |
| 2007/0150223 A1 | 6/2007 | Abraham-Fuchs et al. |
| 2007/0150305 A1 | 6/2007 | Abraham-Fuchs et al. |
| 2007/0150313 A1 | 6/2007 | Abraham-Fuchs et al. |
| 2007/0150314 A1 | 6/2007 | Abraham-Fuchs et al. |
| 2007/0179803 A1 | 8/2007 | Abraham-Fuchs et al. |

OTHER PUBLICATIONS

U.S. Office Action dated Mar. 6, 2014 for related U.S. Appl. No. 13/895,566.

U.S. Notice of Allowance dated Jul. 21, 2014 for related U.S. Appl. No. 13/895,566.

* cited by examiner

METHOD AND SYSTEM FOR MEASURING QUALITY OF PERFORMANCE AND/OR COMPLIANCE WITH PROTOCOL OF A CLINICAL STUDY

This is a divisional of U.S. application Ser. No. 10/975,011 filed on Oct. 28, 2004, which hereby claims priority under 35 U.S.C. §119 on U.S. provisional patent application No. 60/545,164 filed Feb. 18, 2004, the entire contents of which are hereby incorporated herein by reference.

FIELD OF THE INVENTION

The present invention is generally related to the field of clinical studies.

BACKGROUND OF THE INVENTION

The framework for traditional business models for clinical studies has been rather stable over the last few decades. In such a business model, a sponsor (such as a pharmaceutical company which has developed a new drug, for example) paid all participants which performed in the study. At a minimum, these included participating patients and a medical doctor (an investigator) in charge of supervising the patients. In many cases, an investigation or clinical trial site (e.g., a hospital) was additionally included, where one or more investigators was employed.

So-called contract research organizations (CROs) further established their services in the workflow chain of clinical studies, in between the sponsor on one end, and the investigator and patients on the other. The CRO often took over the complete management of the clinical study, including all necessary services including, for example, development of study protocol, recruiting patients and investigators and/or investigation sites, contracting the participants, supervising the conductance of the study, collecting and evaluating data, channeling the payment from the sponsor to the participants, etc. Of course, for such services, the CRO received a substantial part of the aforementioned payment for their own services.

When recruiting the patients, the CRO, or even the sponsor, tended to use and still uses crude methods wherein prospective patients fill out forms and are screened as candidates for clinical studies. The data utilized is normally that obtained from the patient himself or herself. Regarding the investigator or investigator/clinical trial site chosen to conduct/monitor-letc. the study, information previously obtained by the sponsor or CRO was typically used. However, this was often a slow process which often did not produce an ideal patient, investigator and/or investigator/clinical trial site.

Figure 1:
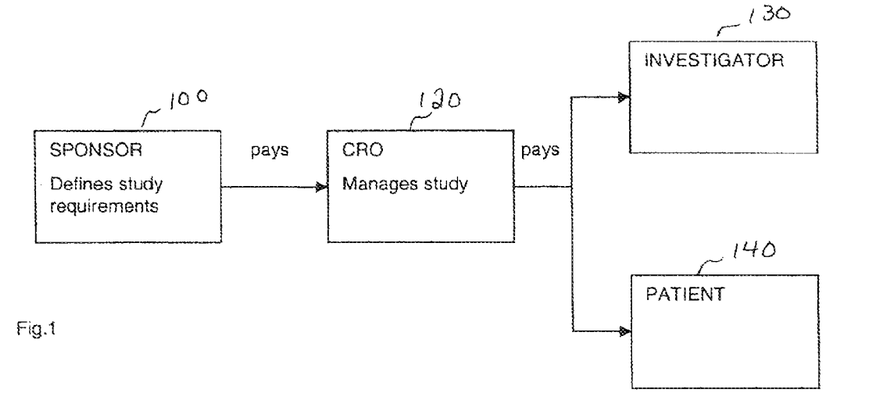
FIG. 1 illustrates a typical traditional model for use in clinical studies.

FIG. 1 illustrates a typical traditional system for use in connection with clinical studies. Initially, a sponsor 100 (such as a drug manufacturer, for example) defines the study requirements or criteria (study parameters, study protocol, etc.) for the particular clinical study in question. A CRO 120 may then be employed to manage the study, noting that the CRO 120 may develop the study requirements or criteria of the clinical study or may assist therein. The CRO may also assist in recruiting patients for the study, as well as selecting an appropriate investigator/investigators and appropriate clinical trial site(s). If a CRO is involved, the CRO is paid by the sponsor 100. The CRO then manages the study and then pays others involved in the study including investigators 130, patients 140, and potentially investigation or clinical trial sites such as hospitals, for example (not shown).

In addition, the quality of the data acquired must be maintained for proper results in clinical trials, and for the ultimate approval of a new drug, for example. Quality of clinical raw data such as medical images or physiological data can to some extent be checked retrospectively (see, for example German application no. DE 10 2004 008 197.2 entitled "Verfahren zur Qualitätskontrolle von je an unterschiedlichen, aber vergleichbaren Patientenkollektiven im Rahmen eines medizinischen Vorhabens erhobenen medizinischen Datensätzen", filed Feb. 9, 2004, the entire contents of which are incorporated herein by reference). However, the quality of a database acquired during a clinical study does not only depend on the inherent quality of the raw data (such as signal noise, the wrong use of the measurement device, miscalibration of the device, etc.), but also depends considerably on the workflow context in which the data had been generated. The "standard operating procedure" (SOP) of a clinical trial also regulates many details of the workflow context in which the patient participating in the clinical study has to be treated. This is part of the quality regulations of a clinical trial.

As previously indicated, the requirements for performing a clinical study may be defined in a study protocol, which may be defined by the sponsor 100 and/or the CRO 120. Although participants in the clinical trial confirm, by signing a contract for example, that they are going to comply with the quality regulations, there is no systematic and/or automated way to check this quality compliance. Due to the inability to measure quality compliance in clinical workflow, the payment to the patients, investigators, CRO, investigator/clinical trial sites, etc. does not depend on quality of data.

SUMMARY OF THE INVENTION

The present inventors have recognized problems with the traditional clinical study model, and an object of the present application is to improve on the traditional clinical study model, and thus improve the clinical study or clinical study process. The present inventors have further recognized a need for objective, and preferably automated, supervision of compliance with quality criteria and/or a need for a systematic and preferably automated way to check quality compliance of a clinical study.

The present inventors have further recognized that the advent of information technology (IT)—based clinical workflow systems and data management systems, such as the products "SOARIAN" or "SYNGO" from Siemens AT medical solutions for example, provide some of the tools which can be used in providing an automated check of quality regulations during clinical workflow in the context of a clinical trial for example. Data management systems like "SYNGO" store and manage not only clinical data and images, but to some extinct, the context in which the data have been generated. For example, in the standardized DICOM header of medical images, facts like the use of contrast agents, for example, are included. The image modality systems, which connect to "SYNGO" and "SORIAN", safe procedures associated with the imaging processes. This, as recognized by the present inventors, permits a new and novel retrospective analysis of the processes as set forth in one embodiment of the present application.

In a similar way, workflow systems like "SORIAN", for example, distribute sub-tasks of clinical workflow to responsible persons, schedule and optimize sequence of actions in a clinical workflow, etc. Thus, as recognized by the inventors, they can be used to automatically report aspects such as, for example, time, place, responsible persons that performed actions, use devices and materials, etc. The present inventors have recognized that this information can be used, in a unique way, to improve quality compliance of a clinical study, and even to improve quality compliance in any type of clinical workplace.

One specific object involves the use of clinical IT infrastructure to derive, when correlated with obtained criteria of a clinical study, a measure of compliance with the clinical study. Further, the criteria for the clinical study may include at least one of patient and non-patient compliance criteria and/or compliance/non-compliance of a clinical trial site. The present inventors have recognized these and other needs for improving a clinical study compliance.

Further, the inventors have recognized that in the traditional setting of a clinical study, the CROs and sponsors 100 had no access to this IT infrastructure. The investigation or clinical trial sites such as a hospital, for example, were the owner of such IT infrastructure and databases. However, as these investigation/clinical trial sites were biased parties and thus sponsors 100 of clinical studies and CROs 120 were not interested in their involvement to the extent of using their IT infrastructure.

The present inventors, in one embodiment of the present invention, have recognized that further value of both existing clinical IT databases storing clinical data, as well as IT-based clinical workflow management systems and data management systems developed by the present assignee, and have thus developed further uses for such systems in the area of clinical study compliance; and even in the area of hospital procedure compliance.

In one embodiment, a method of determining clinical study compliance of the present invention includes receiving (and/or even storing) criteria for the clinical study; accessing (or even storing) clinical data relating to the clinical study; and correlating the criteria and clinical data to determine a measure of compliance with the criteria of the clinical study. The method may further include calculating a measure of compliance for a plurality of criteria for the clinical study.

The measure of compliance can then be used in at least one of, for example, calculating a payment based upon the determined measure of compliance (by a clinical trial site, for example); calculating a ranking (for multiple clinical trial sites, for example); and/or detecting and/or reporting quality problems (during the course of conducting a clinical study, for example). In addition, weighted criteria may be used. This weighted criteria can include weighting that affects the measure of compliance, for example.

In another embodiment, the invention relates to a method of monitoring a clinical study at a trial site, including accessing (or even storing) at least one protocol for the clinical study; accessing (or even storing) clinical data relating to actions performed at the clinical trial site based upon the at least one protocol; and correlating the at least one protocol and clinical data and using the correlated information to monitor the clinical study at the clinical trial site. Such a method can further include determining a measure of compliance of clinical study protocol at the clinical trial site, based upon the correlation, wherein the clinical trial site may be a hospital, for example.

In yet another embodiment, the invention relates to a method of improving compliance within at least one clinical study at a clinical trial site. The method includes obtaining at least one protocol for the clinical study; and planning a plurality of clinical actions in compliance with criteria set forth in the at least one protocol, wherein the planning is performed at least partially automatically. The criteria may include at least one of rules and constraints, and the at least one of rules and constraints may be stored in machine readable form.

Further, the planning may include at least one of scheduling use of equipment at the clinical trial site and scheduling a clinical action item at the clinical trial site.

The present inventors, in one embodiment of the present invention, also recognized the importance of the introduction of some type of quality control and benchmarking measures. By inclusion of various measures, the payment for the clinical study can be made to be performance/outcome oriented, rather than oriented as contracts for upfront fixed amounts.

Other embodiments of the present application may include devices for implementing any of the aforementioned methods, programs adapted to perform any of the aforementioned methods when executed on a computer device, and/or computer readable mediums storing any of the aforementioned programs.

Additional embodiments of the present application may include systems for implementing any of the aforementioned methods.

For a full understanding of the nature and advantages of the various aspects of the invention, reference should be made to the detailed description of exemplary embodiments taken in conjunction with the accompany drawings. The detailed description provides only exemplary embodiments of the invention and thus, the claims of the present invention should not be limited as such.

BRIEF DESCRIPTION OF THE DRAWINGS

The present invention will become more fully understood from the detailed description of preferred exemplary embodiments given hereinbelow and the accompanying drawings, which are given by way of illustration only and are thus not limitive of the present invention, and wherein.

DETAILED DESCRIPTION OF THE
EXEMPLARY EMBODIMENTS OF THE
PRESENT APPLICATION

In one embodiment, the present invention is directed to a method of determining clinical study compliance. The method includes obtaining criteria for the clinical study, and then accessing stored clinical data relating to the clinical study. Thereafter, the criteria and clinical data are correlated to determine a measure of compliance with the criteria of the clinical study. In a further embodiment, a measure of compliance for a plurality of criteria for the clinical study are calculated. The method can be performed utilizing clinical information technology (IT) infrastructure and then, if needed, additional databases can be created.

Clinical data can include data stored in a database of existing clinical IT infrastructure, such as an electronic healthcare database, for example. This can include, but is not limited to at least one of a database with electronic patient records, a database of clinical workflow management system, information from a hospital IT system (financial or clinical), information from a laboratory or radiology information system, information from a picture archiving and communication system (PACS), information from a physician's IT system, for example, etc.

In an embodiment of the present application, use is made of clinical IT infrastructure and databases, such as electronic patient records (EPR), hospital information systems (HIS) and/or clinical workflow management systems. In an embodiment of the present application, such clinical IT infrastructure and databases, storing various types of clinical data, are correlated with obtained criteria for the clinical study, to determine a measure of compliance with the criteria of the clinical study. More specifically, in one embodiment, the system/method of the present application uses this correlation to check on how an investigator/clinical trial site/patient/etc. is complying with various parameters or requirements of a clinical study.

In another embodiment, the present invention is directed to a method of monitoring a clinical study at a clinical trial site. As such, a sponsor of a clinical study can check or monitor how an investigator/patient/clinical trial site, is complying with requirements and/or other criteria of a study. The method can include obtaining at least one protocol for the clinical study; accessing stored clinical data relating to actions performed at the clinical trial site based upon the at least one protocol; and correlating the at least one protocol and clinical data and using the correlated information to monitor the clinical study at the clinical trial site. The method, in one embodiment, can further include determining a measure of compliance of clinical study protocol at the clinical trial site, based upon the correlation.

Figure 2:
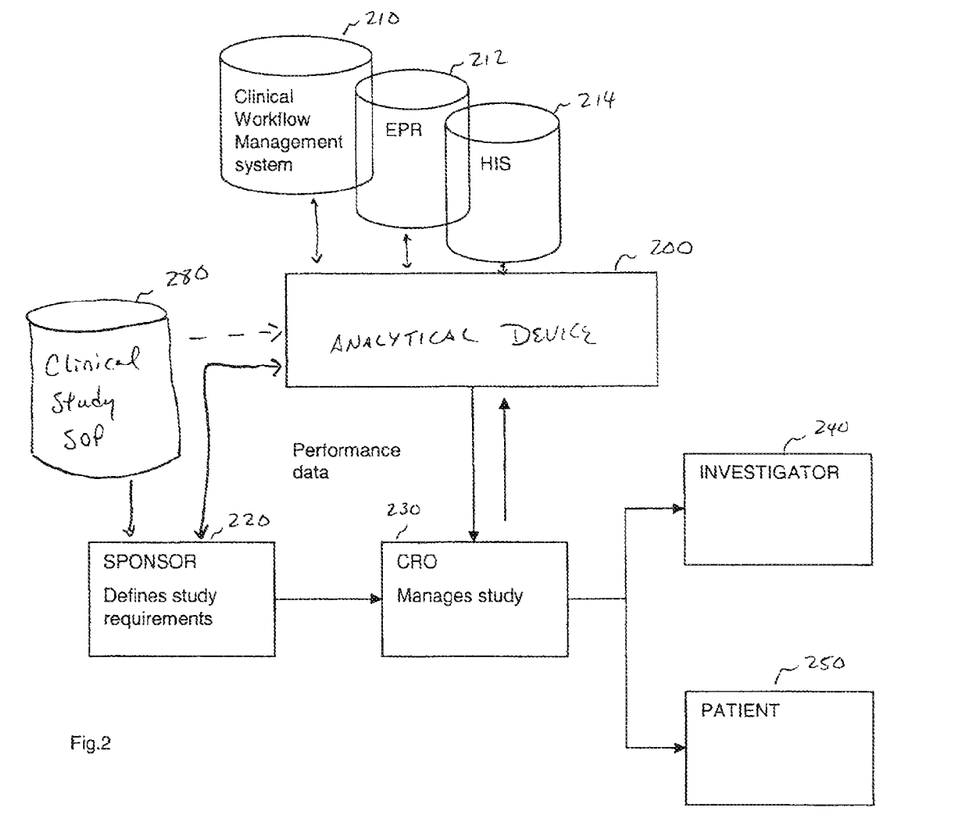
FIG. 2 is an example of an aspect of an embodiment of the present application illustrating the server and its connection to various databases.

As shown in FIG. 2 of the present application, an analytical device 200 has been developed. This analytical device 200 can be a type of computer device/processor and/or server which is networked or otherwise has access to clinical IT infrastructure and which is further networked to, or can otherwise receive criteria regarding a clinical study and receive data with patient identification (e.g. patients name and birthday, or a patient identification code such as a patient social security number), wherefrom a Patient's ID Database is built.

The analytical device 200 then may derive rules from the criteria. These rules may include, but are not limited to, rules which influence the planning of a clinical action, rules which may be applied to check results from a clinical action for their compliance with the criteria, etc. These rules may be converted (if necessary) by the analytical device 200 into a machine-readable form, which can then be interfaced to and understood by, for example, the clinical workflow management system. Then, the rules may be applied, for example, to influence the planning of clinical actions for all patients with Ids contained in the patient ID data base; may be applied to check results of clinical actions involving these patients for there compliance with the criteria; etc.

The analytical device 200 is able to access and analyze clinical data, such as that stored in any of the clinical workflow management system 210, EPR 212, HIS 214 (or any other type of clinical IT infrastructure and/or database). This analytical device 200 connects or is otherwise networked to, and can thereby access/receive/obtain and then analyze data from any of the clinical workflow management system 210, EPR 212, HIS 214 (or any other type of clinical IT infrastructure and/or database). The analytical device 200 may further be networked or otherwise connected to the sponsor 220, the clinical study SOP database 280 and/or the CRO 230. The analytical device 200 can then receive or otherwise obtain criteria for a clinical study from the sponsor 220, clinical study SOP database 280 and/or CRO 230 and can then analyze the obtained clinical data in conjunction with (or based upon) the obtained criteria for a clinical study. The analytical device 200 of an embodiment of the present application is then able to correlate the clinical data in conjunction with (or based upon) the obtained criteria for a clinical study, to determine a measure of compliance with the criteria of the clinical study. Alternatively or in addition thereto, the analytical device 200 is able to use the correlated information to monitor the clinical study at the clinical trial site.

As shown in FIG. 2, the analytical device 200 can receive requirements of the clinical study directly from the sponsor 220, which can include the criteria for the clinical study; and/or can receive such information from the CRO 230 managing the study; noting that the CRO 230 may take on all necessary services for managing the study including, but not limited to development of a study protocol, recruiting patients and investigators and/or investigation or trial sites, contracting the participants, supervising the conductance of the study, collecting and evaluating the data and channeling the data from the sponsor to the participants. Thus, the CRO 230 and/or sponsor 200 may transmit information regarding desired/necessary criteria of the clinical study (and even desired target parameters) to the analytical device 200. Accordingly, the analytical device 200, in some way, obtains access to the information in the clinical study SOP database 280.

Clinical data of a plurality of clinical trial or investigation sites/patients/investigators/etc., and the obtained criteria, may be further analyzed to determine clinical trial or investigation sites which meet or exceed target or thresholds of compliance with the obtained criteria and such plural patients/clinical trial sites/investigators/etc may be ranked accordingly. This ranked information can then be output or otherwise sent to the sponsor 220 and/or CRO 230 for use in determining desired patients/clinical trial sites/investigators/etc. for continued use and/or termination regarding the clinical study.

"Criteria", as referenced throughout the embodiments of the application, refers to clinical study criteria. These "criteria" are important aspects of the clinical study. These criteria of the study can be used by the analytical device 200. Thus, the criteria outline key or other important aspects of the study which, when provided and correlated with clinical data, can help produce measures of compliance of the clinical study that can be used, for example, to monitor the clinical study at the clinical trial site.

Some non-limiting examples of "criteria" may include, but are not limited to e.g.:
Number of patients needed for the clinical study;
Patient inclusion criteria such as, for example, patients with a given diagnosis (e.g., diabetes type I, for example). Another example of patient inclusion criteria can be, for example, age group (e.g., 40-60 years) of patients to be included in the study;
Patient exclusion criteria: Patients not previously diagnosed with an ailment, (hypertension, for example). Another example of patient exclusion criteria can be, for example, patients not having been prescribed with a given medication "x" previously;
Accompanying exams to be undertaken during the study (aside from prescribing the medication under study) to the patient: This can include, but is not limited to regular (i.e., weekly, daily, etc.) control of blood pressure, heart rate, etc.; Making diagnostic images for the therapy success control every "x" days/months/years;
The drug under study has to be taken by the patient 3 times a day, always before the meals (breakfast, lunch, dinner) (med.: pre-prandial medication); etc.

Often, elements relating to these "criteria" cannot be measured directly, but must be deduced from other measurable parameters or clinical data, and perhaps from a combination of other measurable parameters or other measurable clinical data. This may include volatile data which may be entered and/or stored for only a short time, and later deleted or erased. For example, the exact time as to when a patient has taken a drug or eaten his meal is usually not measured and recorded by a nurse. However, this time is typically recorded in the Clinical Workflow Management System when the drug and the meal are scheduled for delivery to the patient. Therefore, the criterion "pre-prandial medication" can at least, to some certainty, be indirectly deduced from the two database entries including "Scheduled time for drug delivery to patient" and "Scheduled time for meal delivery to patient", provided that the patient has taken medication and is eating meals immediately after delivery. As such, an attempt may be made to correlate volatile clinical data with criteria for the clinical study. If so, the volatile data may be permanently stored upon determining a lack of correlation. Also, volatile clinical data may be correlated with criteria for the clinical study, and the volatile data may be permanently stored upon determining that the measure of compliance is below a threshold. Further, clinical data may be stored permanently, upon determining that the data relate to a patient enrolled in the clinical study.

Thus, the analytical device 200 can, for example, build an empirical database for use in such situations, which contains rules on how to combine measurable indirect criteria in order to derive from these, a probability that a non-measurable criterion is met. Accordingly, the analytical device 200 can create a type of mathematical formula or weighting factors regarding the combining of several direct and indirect aspects of the criteria into a weighted combination. Most likely, this formula will include a weighted sum or weighted product of a single criteria. This can then be correlated with existing clinical data from the clinical IT infrastructure to derive a measure of compliance and/or to monitor a clinical study at a clinical trial site, for example. Thereafter, an output ranking may be derived from the calculated/derived performance measures, the ranking being based upon weighted determinations using the weighing factors. Weighted criteria may be used. This weighted criteria can include weighting that affects the measure of compliance, for example. Further, the ranking can be for any or all of single or multiple patients/clinical trial sites/investigators/etc.

The assignee of the present application has further been involved in various other inventions regarding clinical studies, and in some cases the use of clinical IT infrastructure, in order to improve the development of clinical study monitoring and/or compliance; the development of clinical study protocols; improving the effectiveness of patient recruiting; controlling the compliance of clinical study protocol rules; etc. The entire contents of each of the following applications is hereby incorporated by reference in the present application:

"Procedure to Identify Eligible Study Patients in an All-Day Setting" (U.S. provisional application Ser. No. 60/545,169, filed Feb. 18, 2004) and corresponding U.S. non-provisional application entitled "A Method Of Recruiting Patients For A Clinical Study", assigned U.S. application Ser. No. 10/975,059, and filed on Oct. 28, 2004;

"Incentive-System for Clinical Trials" (U.S. provisional application Ser. No. 60/545,170, filed Feb. 18, 2004), and corresponding U.S. non-provisional application entitled "A Method Of Monitoring Patient Participation In A Clinical Study", assigned U.S. application Ser. No. 10/975,056, and filed on Oct. 28, 2004;

"Procedure Providing a Benchmarking of Clinical Test Sites and a Concomitant Method of Quality-Based Monetary Compensation"; (U.S. provisional application Ser. No. 60/545,165, filed Feb. 18, 2004) and corresponding U.S. non-provisional application entitled "A Method Of Examining A Plurality Of Sites for A Clinical Trial", assigned U.S. application Ser. No. 10/975,009, and filed on Oct. 28, 2004;

"Risk-Sharing Business Model for the Use of HIS Data to Improve Cost Effectiveness of Clinical Studies" (U.S. provisional application Ser. No. 60/545,168, filed Feb. 18, 2004) and corresponding U.S. non-provisional application entitled "A Method Of Improving A Clinical Study", assigned U.S. application Ser. No. 10/975,057, and filed on Oct. 28, 2004;

"Quality Compliance Improvement in Clinical Studies using IT-Based Clinical Workflow Systems" (U.S. provisional application Ser. No. 60/545,164, filed Feb. 18, 2004) and corresponding U.S. non-provisional application entitled "Method and System For Measuring Quality of Performance and/or Compliance with Protocol of a Clinical Study", assigned U.S. application Ser. No. 10/975,011, and filed on Oct. 28, 2004;

Verfahren zur Durchührung einer klinischen Studie (DE 10 2004 008 196.4);

Verfahren zur Überprüfung der Durchführbarkeit eines medizinischen Vorhabens mit Aufnahmekriterien für Patienten (DE 10 2004 008 189.1);

Verfahren zur Qualitätskontrolle von je an unterschiedlichen, aber vergleichbaren Patientenkollektiven im Rahmen eines medizinischen Vorhabens erhobenen medizinischen Datensätzen (DE 10 2004 008 197.2);

Verfahren and Einrichtung zur Überprüfung der Einhaltung einer Durchführungsvorschrift für eine an einem Patienten durchgeführte medizinische Maβnahme (DE 10 2004 008 190.5);

Verfahren zur Qualitätsbewertung von elektronisch gespeicherten, insbesondere medizinischen, Wissensdaten (DE 10 2004 008 191.3);

Verfahren zur Auswahl eines möglichen Teilnehmers far ein medizinisches Vorhaben anhand eines Auswahlkriteriums (DE 10 2004 008 192.1);

Verfahren and Informationssystem zur Durchführung einer klinischen Studie an einem Patienten. (DE 10 2004 008 194.8);

Verfahren zur Überprüfung der Einhaltung einer einem medizinischen Arbeitsablauf zugeordneten Durchführungsvorschrift (DE 10 2004 008 195.6); and Verfahren zur Auswahl eines Teilnehmers für ein medizinisches Vorhaben mit Auswahlkriterien für Patienten (DE 10 2004 008 188.3).

In one embodiment of the present invention, further value of such clinical IT databases has been realized, wherein clinical data from a plurality of different investigation sites is used, especially different investigation sites participating in the same clinical study. This information adds to the value that can be provided by the Hospital IT Solution Service Provider, who can develop, sell, install and maintain clinical IT solutions and databases, and in many cases can also store and maintain related databases obtained from a correlation of the traditional clinical IT databases and clinical study criteria.

Thus, it should be understood that FIG. 2, and each of the figures and embodiments of the present application, represents the Hospital IT Solution Provider (for manual data access) or the analytical device 200 (for automated data access) with access to the clinical workflow management system 210, an EPR 212 and/or an HIS 214 of one, or of a plurality of clinical trial sites. Thus, the clinical data can include data from a plurality of clinical trial sites, and further can include data from a plurality of previously conducted clinical trials. Clinical data from a plurality of clinical trial sites is thereby preferably further analyzed in conjunction with the obtained criteria for a clinical study, to determine clinical trial sites which may provide prospective services (for planning, etc.) and to monitor compliance with criteria of an existing study in a more retrospective manner. The names of clinical trial sites can then be provided to the sponsor 220 and/or can be ranked accordingly.

Further, the criteria for the clinical study can include both measurable parameters and parameters of context. Some examples of measurable parameters can include, but are not limited to: number of times a certain exam has been carried out, maximum blood pressure of patient during one day, number of calories of daily diet for a patient, etc. Thus, they are things that can be measured. "Parameters of context" include parameters of context within a clinical workflow chain or clinical action item. For example, a "parameter" like "breakfast for patient X is scheduled for 8:00 am on August 10" is probably not meaningful by itself. But if an MR exam is scheduled at 7 am, which necessitates fasting of the patient before the exam (med.: prae-prandial exam), then the breakfast scheduled at 8 am would be "compliant" in this context. Accordingly, a breakfast scheduled at 6 pm would be non-compliant, and an according MR exam under these circumstances be of much lower or no value.

An advantage that the analytical device 200 can offer, is access to clinical data such as patient data, clinical workflow data, etc., much earlier than the CRO 230, who receives only bundled data in the form, typically, of milestone reports. An analytical device 200 has access to the relevant clinical data in real time, and can extract and update all information on study-relevant clinical data such as patient data, on a daily basis for example. To this end, new software modules can also be incorporated by the Hospital IT Solution Provider into a clinical workflow management system 210, new data entries in the EPR database 212, etc., in order to specifically collect information on a clinical study, and/or to support or enable the analytical device 200 to do such data collection automatically. With the use of such real-time data, a much more effective monitoring of the clinical study compliance and the achievement of clinical study milestones is possible.

Figure 3:
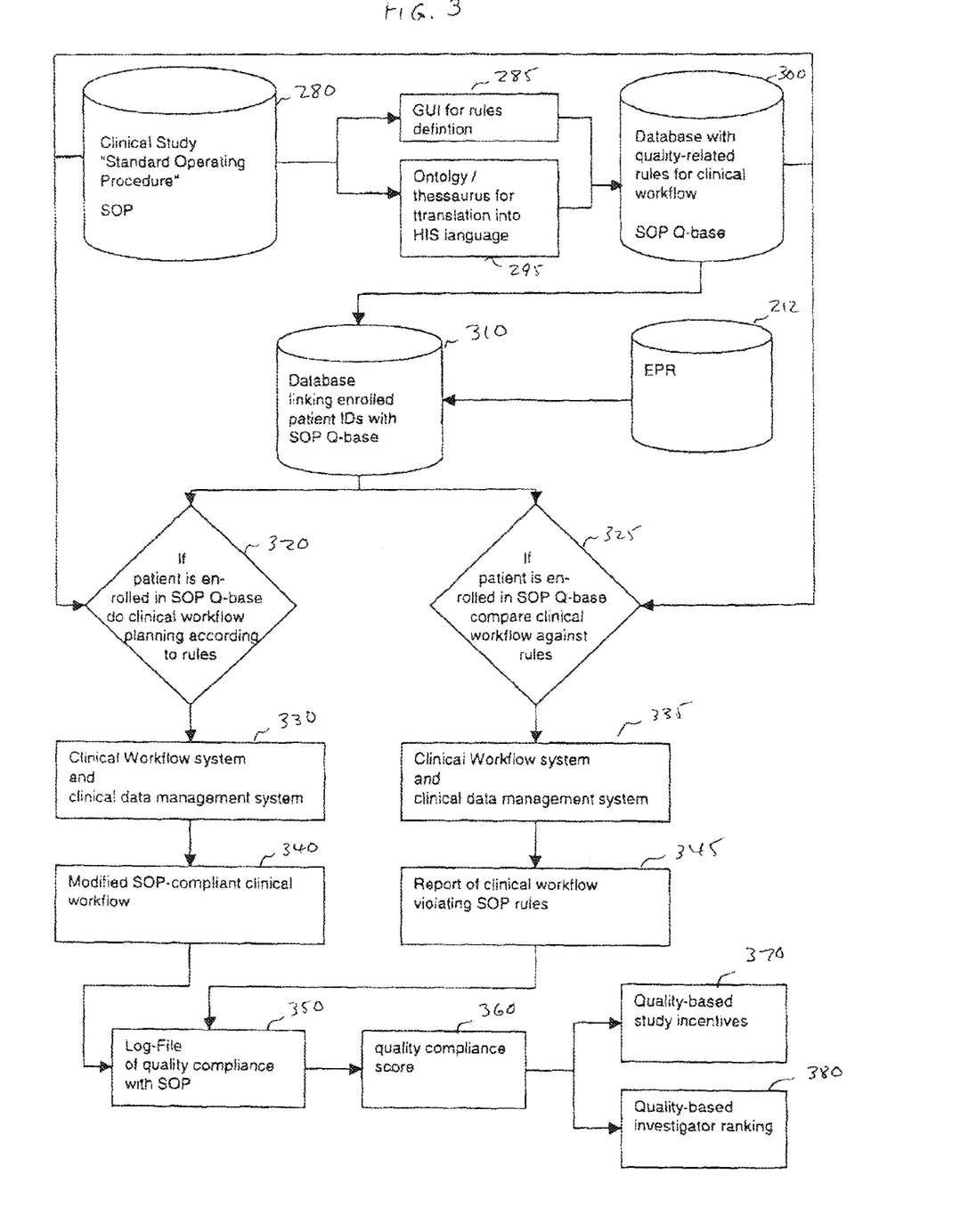
FIG. 3 includes an exemplary embodiment of the overall process of various aspects of the present application.

FIG. 3 provides an illustration of various detailed aspects of embodiments of a method of determining clinical study compliance, and a method of monitoring a clinical study of the clinical trial site. Initially, the analytical device 200 (not shown) obtains criteria for the clinical study, which may include at least one protocol for the clinical study for example. This can be achieved by accessing the clinical study "standard operating procedure" (SOP) information from a database 280, for example. The criteria for the clinical study may be translated into rules which are machine-readable by the clinical workflow management system 210 for example and/or other aspects of the analytical device 200, wherein applicable criteria may be selected from the database 200 using a graphical user interface (GUI) 285 for example. Alternatively, the criteria for the clinical study may be automatically translated into rules which are machine-readable by the clinical workflow management system 210 for example, or by other aspects of the analytical device 200 including at least one of a look-up table, a thesaurus, an ontology, etc. Further, the criteria for the clinical study may be translated into rules which are machine-readable, wherein applicable criteria are selected from a database.

Thus, in monitoring our clinical study for aspects or measures of quality and/or compliance with various protocol rules of the clinical study criteria, parameters of the clinical study criteria may be examined. These can include, but are not limited to, abilities of an investigator and/or investigation site to perform certain tasks, the suitability of clinical processes and the context of clinical rules or parameters of a clinical study, etc. It should be noted that "compliance" as used throughout the present application refers to a measure of compliance with various criteria including rules, protocol, etc. and in some instances, it can be a measure of "quality" (quality criteria, quality improvement, quality assurance, etc.) of performance which is essentially monitored.

From the clinical study SOP 280 as shown in FIG. 3, a list of work-oriented quality regulations may be extracted. These quality regulations, once extracted, can then be formed into a new database for quality-rated rules for clinical workflow known as the SOP Quality Data Base 300 (SOP Q-Base 300), as shown in FIG. 3. Some examples of workflow-flow oriented quality regulations can include, but are not limited to:

patient examinations with examination Z being done at least 5 times per week, but maximally 7 times per week;

a restriction that chemicals used in investigation X are not older than 3 months;

a restriction that bio-chips used within device Y include a serial number higher than XXX; etc. Such a SOP Q-Base is accessible by analytical device 200 and thus can be interconnected, in some manor, with clinical workflow management system 210, EPR 212, HIS 214, etc.

In connection with the various embodiments of the present application, different types of validation of the quality criteria of a clinical study, including but not limited to determining measures of compliance with criteria of a clinical study and monitoring other aspects of the clinical study and the clinical trial site, can include both prospective and retrospective quality checks. In a retrospective quality check, clinical data, including but not limited to clinical actions for example, relating to a clinical study, may be correlated with criteria of the clinical study to determine a type of quality check and/or a measure of compliance with the criteria of the clinical study. In a prospective embodiment of the present application, at least one protocol for the clinical study may be obtained, and a plurality of clinical actions in compliance with the criteria set forth in the at least 1 protocol may be planned, wherein the planning is performed at least partially automatically. Both aspects or embodiments of the present application will be discussed hereafter in conjunction with FIG. 3.

For both modes of operation, both retrospective and prospective, once the criteria for the clinical study is obtained from database 280, the SOP Q-Base 300 may be established in a manor previously set forth. Further, a look-up table of analytical device 200, for example, may be used to link required information regarding patients enrolled in the clinical study and may be able to obtain this information from existing databases including but not limited to HIS 214 at a clinical investigation site. To this end, a list of enrolled patient IDs, regarding patients enrolled for a particular clinical study, may be attached or entered into the related SOP Q-Base as shown in element 310 of FIG. 3. Alternatively, a SOP Q-Base ID may be entered into the patient's EPR database 212, for example, for identify a clinical study SOP belonging to the clinical study in which the patient is participating.

Elements 320 and 325 deal with the prospective and retrospective aspects of the present application. As shown in element 320, if a patient is enrolled in the SOP Q-Base 300 for example, clinical workflow planning can be done in accordance with at least one of criteria directly obtained from the clinical study SOP 280 and/or rules for clinical workflow established in the SOP Q-Base 300. In such an embodiment of the present application, a method for improving compliance with at least one clinical study of the clinical trial site can be achieved. The method can include obtaining at least one protocol for the clinical study from the clinical study SOP database 280 for example, including but not limited to rules for clinical workflow established by the SOP Q-Base 300. Once obtained, a plurality of clinical actions can then be planned in compliance with the criteria set forth in the at least one protocol, wherein the planning may be performed at least partially automatically.

More preferably, the SOP Q-base 300 may be automatically contacted by the clinical workflow management system 210. A clinical action may be planned, scheduled, required, etc. by the analytical device 200 in conjunction with the clinical workflow management system 210 for example. For example, the method of at least one of planning and scheduling a clinical action can include obtaining criteria for a clinical study and for at least one clinical action associated with the clinical study and accessing stored clinical data relating to the clinical study. Thereafter, the criteria and clinical data may be correlated to at least one of plan and schedule the clinical action.

The analytical device 200 can then automatically take into account any restriction defined in the SOP Q-Base 300 or in at least one protocol of a clinical study from database 280, wherein this can be done for particular clinical study participants. Accordingly, it can then modify the required clinical action. Optionally, any modification of clinical workflow caused by SOP restriction may be documented such that it can later be justified as to why this clinical workflow situation deviated from normal procedures. This can be done by documenting such information in an electronic patient record (EPR) 212 together with an SOP ID (name, etc.), for example.

The criteria of the at least one protocol of the at least one clinical study may include rules and/or constraints. The rules and/or constraints may be stored in machine readable form, such as in the SOP Q-Base for example. The planning may include, but is not limited to, at least one of scheduling use of equipment at the clinical site, use of personnel at the clinical trial site, scheduling a certain sequence of subsequent clinical actions, etc. Thus, planning in a clinical trial site, such as a hospital, can take place at least partially automatically, including at least one of the scheduling of use of equipment, the planning of use of personnel, and scheduling a certain sequence of subsequent clinical actions, etc. Further, the at least one of planning and scheduling can include at least one of planning and scheduling at least one subsequent clinical action.

In general, a clinical workflow management system coordinates clinical services across team members and institutions. It permits the planning, execution, and tracking of clinical actions, and documents and reports the clinical actions performed. For planning and scheduling actions, a workflow engine, a rules engine and definitions database are used to identify the relevant sets of tasks or to identify workflow failure events that require workflows to be reconfigured (e.g., drug in conflict with patient allergy). This part of a clinical workflow management system is, in other contexts, also referred to as a database of machine-readable clinical guidelines. Furthermore, a resources database for clinical equipment and clinical personnel (including description of roles and responsibilities for each person) is used. Documentation of results from clinical actions, which may include e.g. diagnostic results, diagnostic images, therapeutic decisions, or financial data on incurred cost, reimbursement IDs etc., is generally done in databases such as Hospital Information Systems (HIS), Radiology Information Systems (RIS), and Electronic Patient Record (EPR). Clinical workflow management permits intentional and optimized workflow process designs, and enforces the execution of these designs. They track the progress of individual work steps, and can automatically escalate failed or expired work steps.

For planning the sequence of action steps of a clinical task, and scheduling of all of these steps (including assignment of equipment used and responsible persons), the workflow engine receives a request for an action on a certain patient, for example (such as MR diagnosis of brain for patient with patient ID XXX, for example). The workflow engine accesses the definitions database to identify the action sequence to be planned for this request and how it must fit with other existing or planned action sequences, and accesses the resources database in order to assign and schedule equipment and personal. The rules engine accesses the rules for how specific actions must be modified based on patient and environmental factors. Workflow control is done e.g. by supervising that required output from an action step has been entered into the system, before a subsequent action or a decision point is triggered, which depends on the output of that preceding action. Action steps performed and not performed can be saved historically for subsequent process mining and feedback to adjust and further optimize established action sequences. Thus, in summary, the main parts of a Clinical Workflow Management System are a workflow engine, a rules Engine, and a database on clinical resources.

In the context of optimizing the quality of performance of a clinical study through the use of a Clinical Workflow Management System, essentially requests for clinical actions or requirements constraints on clinical actions for a patient enrolled in a clinical study are taken from the SOP. From these SOP requirements, requests are generated, preferably in a machine-readable form, which are fed into the Clinical Workflow Management System. From this input, the Clinical Workflow Management System plans and schedules clinical actions, or respectively modifies already planned and scheduled clinical actions such that they are compliant with the constraints defined by the SOP.

In the context of embodiments of the invention, the task of extracting requirements for clinical actions from the SOP and feeding them into the Clinical Workflow Management System may either be done manually by a person who represents the role of the Hospital Information Service Provider (HISP) in the business and workflow model described, or it may preferably be achieved automatically by software embedded in the analytical device 200, which analyzes the SOP, extracts requirements, and feeds them into the Clinical Workflow Management System.

Accordingly, as shown in FIG. 3, in this prospective aspect of an embodiment of the present application, planning occurs in element 320; and can be done utilizing the clinical workflow management system database 210 and the analytical device 200, as shown in element 330, for example. As such, a modified SOP—compliant clinical workflow may be established in element 340.

In the retrospective quality check and/or compliance measurement aspect of the present application, clinical workflow or other data can be compared against rules or other aspects/criteria of the clinical study, after the workflow has been executed or the data been measured and documented. This can also include involvement of a clinical workflow system and clinical data management system 210 as shown in element 335, and the report of clinical workflow which violates the SOP rules or other criteria for the clinical study can be established as shown in element 345. As such, a method of checking on quality, and/or determining a measure of clinical study compliance can include obtaining criteria for the clinical study from either SOP database 280 and/or created SOP Q-Base 300. Stored clinical data from databases 210, 212, and/or 214 for example, can be accessed if related to the clinical study, or at least databases can be accessed for patients enrolled in a particular clinical study for example. The criteria of clinical data can then be correlated to determine a measure of compliance or measure of quality regarding the criteria of the clinical study. Further, the clinical data may be stored in association with identification information of patients enrolled in the clinical study, wherein only clinical data relating to patients enrolled in the clinical study are correlated with the criteria.

Further, the retrospective quality check aspect of the present application can be used in a method of monitoring the clinical study of the clinical trial site, wherein at least one protocol for the clinical study can be obtained from at least one of databases 280 and 300 for example; clinical data relating to actions performed at the clinical trial site can be accessed from clinical workflow management system 210 for example, based upon the at least one protocol; and the at least one protocol and the clinical data can be correlated, wherein the correlated information can be used to monitor the clinical study at the trial site.

Thus, the retrospective quality check of the present application can check all reported clinical actions of clinical data, which belonged to a patient ID of a clinical study participant for example, by cross-checking these clinical actions and/or clinical data against protocol, criteria, etc. from the SOP database 280 and/or rules for clinical workflow established by the SOP Q-Base 300. In the case that a threshold of quality is not met, and/or a threshold measure of compliance is not reached for example, such a problem can be automatically reported to the sponsor 220 for example. This can be done by, for example, the sending of an electronic message. Alternatively, this information can be accumulated and reported at a later date. Optionally, a responsible person at the investigator's site or clinical trial site may be notified, such that an action can be corrected and the quality and/or compliance can be maintained.

It is important to note that normally, clinical action information available on the clinical workflow management system 210 is not documented for a long period of time. For example, it is not normally documented as part of the electronic patient record (EPR) and stored in EPR 212. Rather, much of this information is volatile and used only in the system until a clinical action is concluded. Therefore, the cross-check or correlation of clinical actions and/or clinical data with protocol and/or criteria of a clinical study are done in a fairly automated and substantially real-time manor during execution of the clinical workflow, "substantially real-time" meaning that the correlation is done at some point before the volatile data are deleted. Alternatively, and/or additionally, workflow information of a patient enrolled in the clinical study may be stored on a long-term basis in a separate file, for later off-line evaluation against clinical study criteria for example. Thus, when an attempt is made to correlate volatile clinical data with criteria for the clinical study and/or parameters of the clinical study, the volatile data may be permanently stored upon determining a lack of correlation or measure compliance below a particular threshold for example. Further, volatile clinical data may be correlated with criteria for the clinical study, wherein the volatile data are thereafter permanently stored upon determining that the measure of compliance is below a threshold.

In either aspect of a prospective embodiment of the present application or a retrospective quality check of the present application, a log file of quality and/or measures of compliance with protocol and/or criteria of the clinical study may be developed as shown in element 350. This log file of quality checks and/or quality related clinical action planning or clinical action modification may then be delivered to the sponsor 220 of the clinical study. In addition, and/or alternatively, based on such a log-file, a quality and/or compliance score may be calculated in element 360.

Thus, a method of analyzing quality of a clinical study can include creating a database including quality related aspects from criteria for the clinical study, and accessing stored clinical data relating to the clinical study. Thereafter, the method can include correlating the quality related aspects of criteria and clinical data to determine a quality and/or compliance score. The score may then be used to activate quality based studying centers as shown in element 370 for example, in dependence of the achieved quality and/or compliance; and/or can be used for ranking investigators and/or clinical trial or investigator sites according to their quality and/or compliance scores as shown by element 380. This may be especially meaningful if the quality/compliance of several investigators and/or investigator sites is to be compared, all using the same or comparable clinical workflow systems. The log-file and/or the derived score may be communicated to the sponsor 100, for example in repeated intervals throughout the clinical study period, for detection of any quality-related changes.

The SOP regulation or other criteria and/or protocol of the study from database 280 can be translated automatically into the "language" that the analytical device 200 or clinical workflow system understands utilizing an ontology, thesaurus, etc. Alternatively, if this is not possible and must be solved interactively, then the necessary workload can be reduced by building a database with typical SOP rules. Such rules can include but are not limited to, for example, taking a blood sample/urine sample at a pre-determined time (in the morning, fasting, etc.) and handling it according to defined specifications; applying medication (in dose for example) at specific times corresponding to the patient's status, which is interconnected to an understood clinical workflow systems or analytical device 200; etc. The database may include a GUI with a checklist, for example, wherein the user can check a box for each rule, relevant for the current SOP Q-Base SOP Q-Base 300 to be implemented. This checklist will automatically grow with each new implemented SOP, by adding new rules to the list as needed.

In another embodiment, a method can be performed for analyzing quality of a clinical study. Such a method includes creating a database including quality related aspects from criteria for the clinical study, such as the SOP Q-base, for example. Thereafter, the analytical device 200 for example, may access stored clinical data relating to the clinical study. Finally, the quality related aspects of criteria and clinical data may be correlated to determine performance of the quality related aspects of the criteria of the clinical study. Such a method can further include, for example, calculating a measure of performance for a plurality of criteria for the clinical study.

As stated previously, analytical device 200 may access, for example, IT-based clinical workflow systems and clinical data management systems for automated control of quality regulations of clinical studies. A database of machine-readable rules, defining quality related reaulations from criteria/protocol of the clinical study, may be derived from the standard operating procedure document (SOP) of the clinical study 280. Such a database, which can include SOP Q-Base 300 for example, may then be automatically interrogated by the analytical device of the clinical workflow system 200, and deviation from procedures or other aspects of non-compliance may be documented, wherein the rules may automatically be used to modify the clinical workflow according to the requirements of the clinical study. This can enable, for example, objective, quantified and automatic measurement of documentation of quality/compliance in clinical studies; quality-oriented payment of study incentive; ranking of investigator/clinical trial site according to their quality/compliance, etc.

In one embodiment, a first electronic database is built by the analytical device 200. This database, which can include SOP Q-base 300 for example, may be built from criteria for the clinical study (rules, values, thresholds, etc.) either automatically or manually via a GUI, extracting this information from clinical study criteria and/or protocol of database the clinical study SOP 280, for example.

The criteria can include various target quality measures, wherein clinical data of a plurality of clinical trial sites and the obtained criteria for the clinical study may be further analyzed to determine clinical trial sites which may exceed target quality measures of the obtained criteria. From various actual quality measures obtained, a ranking of the quality measures can be derived, wherein the ranking is for at least one of clinical trial sites, payment amounts and study discontinuation decisions (namely, decisions as to whether or not a clinical study should be discontinued). In addition, the determined measure of compliance, as discussed in any of the aforementioned embodiments, may be used in at least one of: calculating a payment based upon the determined measure of compliance; calculating a ranking of compliance for a plurality of clinical trial sites, and at least one of detecting and reporting quality compliance problems during a clinical study.

Thus, the analytical device 200 may suggest discontinuation of the study if one or more of the quality measures, rules, values and thresholds is not met. This discontinuation of a clinical study at a particular clinical trial site, for example, may result in a large reduction in losses or costs which may have been incurred if the study had been continued and unfavorable results were achieved. Thus, this can be a large cost savings to the sponsor 220 and thus the analytical device 200 may receive a contracted percentage of money not spent on a probably unsuccessful study.

Again, in this embodiment, the criteria can include study protocol of the clinical study, wherein the clinical data may be obtained from at least one electronic healthcare database including at least one of those previously set forth. The criteria can include at least one of rules, values and thresholds.

Each of the various embodiments discussed above can include the use of weighting factors. For example, the clinical study criteria obtained can include weighing factors, wherein the weighting factors may reflect a likelihood of the "criteria" to correlate with direct benefit, such as financial benefit, for example. Thus, weighted criteria may be used. This weighted criteria can include weighting that affects the measure of compliance, for example. With regard to protocol/parameters of clinical study criteria such as study duration, costs, study result reliability, major "criteria" which may help to influence these measures positively may include, but are not limited to e.g.:

Overall number of patients which can be controlled in the study, respectively number of patients per time unit which can be enrolled;

Time-effectiveness of data collection and evaluation;

Compliance of investigator and patient with the study rules;

Experience/capability of the investigator to motivate patients for continued participation until the end of the study, and not drop out earlier;

Claimed amount of compensation from investigator and patient, etc.

Often, this "criteria" cannot be measured directly, but must be deduced from other measurable parameters, and perhaps from a combination of other measurable parameters. Thus, the analytical device 200 may, for example, build an empirical database on typical "dropout" rates of patients, wherein these rates might vary with investigation sites, patient's age, geography, etc. Thus, the analytical device 200 can create a type of mathematical formula or weighting factors regarding the combining of several direct and indirect criteria. Most likely, this formula will include a weighted sum or weighted product of the single criteria. Accordingly, an output ranking may be derived and the ranking may be based upon weighted determinations using the weighing factors.

Throughout various aspects and embodiments of the present application, correlation of criteria and/or protocol of a clinical study with clinical data (which can include patient data, reported clinical actions, etc.) is discussed. One exemplary aspect of how such correlation may be achieved, noting that the embodiments are not limited as such, is as follows.

The clinical study criteria includes protocols which may contain, for example, rules and/or constraints regarding the clinical study procedures. These can include, but are not limited to, e.g.:

do blood pressure check at least twice daily, e.g. in the morning and in the evening;

do not subscribe medication X to clinical study patients;

when patient's blood pressure exceeds value Y, reduce dose of medication Z by 50%;

patient's diet must not exceed 2000 Kcal per day.

Correlating the stored clinical study criteria (e.g. these rules and constraints) with clinical data refers to, for example, comparing these rules and constraints (which are stored preferably in a machine-readable form) with clinical data including, but not limited to data entries in the Electronic Patient Record (EPR) 212; input and output parameters for clinical actions in clinical workflow management system 210 for example; etc. From such a comparison, it can then be determined from these EPR workflow management and/or other clinical data, whether or not the rules, for example, of the protocol/criteria of the clinical study have been met. In simple cases, the "measurement for correlation" may be e.g. a 1 if the rule is met, and a zero, if the rule is not met. The compliance with some rules may also be measured in a more quantitative way, e.g. for the rule "patients diet must not exceed 2000 Kcal/per day" can be measured with 100% for all diets less or equal to 2000 Kcal/per day, and being 90% for 2200 Kcal, 50% for 3000 Kcal etc. Thus, a measure of compliance may be determined. Further, the correlated information can be used to monitor the clinical study at the clinical trial site; and/or at a plurality of clinical trial sites.

Compliance, as used throughout the embodiments of the present application, refers to participants of the clinical study (investigator, patient, clinical trial site, etc.) are following the rules and constraints defined in the study protocol/criteria of the clinical study. The most important example for compliance is certainty, e.g. that a medication under test has to be taken by the patient exactly in the prescribed manner (number of pills and times of day when the medication has to be taken, before or after meals, taken together with a minimum amount of liquid, etc.). The embodiments of the present application include both patient compliance (and/or patient non-compliance) and investigator/clinical trial site compliance to follow the protocol rules; and further include analysis of the skills and ability of the investigator to perform certain tasks, and the suitability of clinical processes in the context of these protocol rules. For example, a physician with limited experience in Ultrasound exams may well be compliant with all rules to the best of his knowledge, but still may deliver inferior results as compared to a very experienced colleague. For these reasons, compliance also includes "quality criteria", "quality improvement", and/or "quality assurance".

One non-limiting example of the methodology of an embodiment of the present application is as follows. Again, this is a non-limiting Illustrating example.

In this non-limiting example, a patient in a hospital is enrolled in a clinical study. The protocol of the clinical study, obtained as criteria of the clinical study includes:

A) the patient's blood pressure is measured at least 3 times daily, between 6-8 am, 12-2 pm, and 18-20 pm respectively, and B) that an ultrasound exam is performed once weekly, with the patient being in a fasting condition The clinical data, which may be accessed using a patient ID of the participating patient for example, is correlated with the relevant clinical protocol, e.g. by entering a reference to the clinical protocol rules database (SOP Q-Base 300) in the patient's EPR 212. Then the SOP Q-Base 300 is analyzed by the analytical device 200 for applicable rules. When rule (A) is identified, the clinical action "blood pressure measurement" is scheduled or planned at least partially automatically each day according to the rules, and appropriate human resources provided (in the prospective planning aspect).

The results of the blood pressure measurement, together with time and date of the exam, are then entered into the patient's EPR 212. This data may then be analyzed periodically and extracted into the patients study log-file, for example. In case that measurement values are missing, or are not taken within the defined time frame, this fact may be logged and/or automatically reported e.g. to the sponsor 220 (e.g. if the deviations exceed a predefined threshold).

When rule (B) is encountered, weekly ultrasound exams are scheduled or planned for the patient, at times preceding the scheduled breakfast, such that the patients is in a fasting condition. The rule is entered into the patient's EPR 212, such that any possible rescheduling of a specific ultrasound exam is preferably only done in combination with according scheduling of the breakfast on this day. Times of actually carried-out exams may be recorded in the EPR 212, optionally together with the delivery time of the breakfast, such that retrospective check of rule compliance may be carried out in addition to this prospective clinical workflow planning.

Number and severity of deviations from these rules may then automatically calculated from the entries in the patient's EPR 212, for example. For each rule, a compliance measure may then be calculated from the sum of all deviations from this rule for example. Alternatively, or optionally, for all rules together a combined measure is calculated to quantify the overall quality of this patient's participation in the study. If the individual or combined quality measures are exceeding predefined thresholds, predefined actions may automatically be taken, such as excluding the patient from the study, excluding the clinical trial site from the study, reducing the payment for the clinical trial site negotiating action plans how to improve the performance of the trial site, etc.

A method of improving compliance within at least one clinical study at a clinical trial site can thus include obtaining at least one protocol for the clinical study, and planning a plurality of clinical actions in compliance with criteria set forth in the at least one protocol. The planning may be performed at least partially automatically, wherein the criteria includes at least one of rules and constraints. At least one of rules and constraints may be stored in machine readable form.

Further, the planning may include at least one of scheduling use of equipment at the clinical trial site and/or at least one of scheduling use of personnel at the clinical trial site. Additionally, the clinical trial site may be a hospital.

Any of the aforementioned methods may be embodied in the form of a system or device, including, but not limited to, any of the structure for performing the methodology illustrated in the drawings. Such structure may include, for example, a database, storing criteria for the clinical study. Further, it may include one or more devices for accessing stored clinical data relating to the clinical study, and for correlating the criteria and clinical data to determine a measure of compliance with the criteria of the clinical study. In another embodiment, the system may be for monitoring a clinical study at a clinical trial site, and may include one or more devices for obtaining at least one protocol for the clinical study; for accessing stored clinical data relating to actions performed at the clinical trial site based upon the at least one protocol; and for correlating the at least one protocol and clinical data and using the correlated information to monitor the clinical study at the clinical trial site. In yet another embodiment, the system may be for improving compliance within at least one clinical study at a clinical trial site and may include one or more devices for obtaining at least one protocol for the clinical study; and for planning a plurality of clinical actions in compliance with criteria set forth in the at least one protocol, wherein the planning is performed at least partially automatically. Further, in still another embodiment, the system may be for creating a database including quality related aspects from criteria for the clinical study. The system may include one or more devices for accessing stored clinical data relating to the clinical study; and for correlating the quality related aspects of criteria and clinical data to determine performance of the quality related aspects of the criteria of the clinical study.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or removable medium arranged so that it can be separated from the computer device main body. Examples of the built-in medium include, but are not limited to, rewriteable involatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable involatile memory, such as memory cards; and media with a built-in ROM, such as ROM cassettes.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method of improving compliance within at least one clinical study at a clinical trial site using an analytical device having a processor, the analytical device being networked to clinical information technology (IT) infrastructure, the clinical IT infrastructure including a clinical workflow management system, comprising:

obtaining, by the analytical device, at least one protocol for the clinical study by accessing a clinical study standard operating procedure (SOP) information from a first database;

extracting, from said first database, a list of work-oriented quality regulations that includes weighting factors indicating a weight given to an associated one of the quality regulations based on a correlation between the associated quality regulation and an increase in the compliance with the at least one clinical study provided therefrom, and forming said quality regulations including the weighting factors into a second database for quality-related rules for a clinical workflow;

linking, by said analytical device, enrolled patient identifications (IDs) with said second database;

planning, by said analytical device in conjunction with the clinical workflow management system, if a patient is enrolled in the second database, a plurality of clinical actions in compliance with criteria obtained from the clinical study standard operating procedure (SOP) information of said first database and/or from the quality-related rules for the clinical workflow established in said second database; and deleting volatile clinical data generated during execution of the clinical actions upon determining a correlation between the volatile clinical data and the criteria.

2. The method of claim 1, wherein the criteria includes at least one of rules and constraints.

3. The method of claim 2, wherein the at least one of rules and constraints are stored in machine readable form.

4. The method of claim 1, wherein the planning includes at least one of scheduling use of equipment at the clinical trial site.

5. The method of claim 1, wherein the planning includes at least one of scheduling use of personnel at the clinical trial site.

6. The method of claim 4, wherein the clinical trial site includes a hospital.

7. The method of claim 1, further comprising:
calculating, by the analytical device, a measure of compliance of a plurality of criteria from the at least one protocol for the clinical study.

8. The method of claim 7, wherein the measure of compliance includes clinical trial site compliance.

9. The method of claim 1, wherein the at least one protocol includes patient compliance criteria and clinical trial site compliance criteria.

10. The method of claim 1, wherein the at least one protocol for the clinical study includes weighted criteria, wherein the weighting affects the compliance.

11. The method of claim 1, wherein the at least one protocol for the clinical study includes measurable parameters and parameters of context.

12. A system for improving compliance within at least one clinical study at a clinical trial site, comprising:

an analytical device having a processor; and clinical information technology (IT) infrastructure networked with the analytical device, the clinical IT infrastructure including a clinical workflow management system, wherein the analytical device is configured to, obtain at least one protocol for the clinical study by accessing a clinical study standard operating procedure (SOP) information from a first database, extract, from the first database, a list of work-oriented quality regulations that includes weighting factors indicating a weight given to an associated one of the quality regulations based on a correlation between the associated quality regulation and an increase in the compliance with the at least one clinical study provided therefrom, and form the quality regulations including the weighting factors into a second database for quality-related rules for a clinical workflow, link enrolled patient identifications (IDs) with the second database, plan, in conjunction with the clinical workflow management system, if a patient is enrolled in the second database, a plurality of clinical actions in compliance with criteria obtained from the clinical study standard operating procedure (SOP) information of said first database and/or from the quality-related rules for the clinical workflow established in said second database, and delete volatile clinical data generated during execution of the clinical actions upon determining a correlation between the volatile clinical data and the criteria.

13. The system of claim 12, wherein the criteria includes at least one of rules and constraints.

14. The system of claim 13, wherein the at least one of rules and constraints are stored in machine readable form.

15. The system of claim 12, wherein the planning includes at least one of scheduling use of equipment at the clinical trial site.

16. The system of claim 13, wherein the planning includes at least one of scheduling use of personnel at the clinical trial site.

17. The system of claim 15, wherein the clinical trial site includes a hospital.

* * * * *